United States Patent [19]

Staub et al.

[11] Patent Number: 5,112,849
[45] Date of Patent: May 12, 1992

[54] FUNGICIDAL USE OF A CYANOPYRROLE DERIVATIVE AND METHOD FOR PRODUCING SAME

[75] Inventors: Theodor Staub, Riehen; Heide Dahmen; Robert Nyfeler, both of Basel; Robert J. Williams, Schönenbuch, all of Switzerland

[73] Assignee: Ciba-Geigy Corporation, Ardsley, N.Y.

[21] Appl. No.: 526,773

[22] Filed: May 18, 1990

Related U.S. Application Data

[63] Continuation of Ser. No. 18,689, Feb. 25, 1987, abandoned.

[30] Foreign Application Priority Data

Mar. 4, 1986 [CH] Switzerland .............................. 865/86

[51] Int. Cl.$^5$ ............................................. A01N 43/36
[52] U.S. Cl. ..................................................... 514/427
[58] Field of Search ......................................... 514/427

[56] References Cited

U.S. PATENT DOCUMENTS

4,546,099  6/1985  Nyfeler ................................. 514/427

FOREIGN PATENT DOCUMENTS

2024824  1/1980  United Kingdom .

OTHER PUBLICATIONS

Derwent Abstracts Oct. 7, 1981, No. 59691D.
Chem. Abstracts C.A. 105:60520r.

*Primary Examiner*—Allen J. Robinson
*Attorney, Agent, or Firm*—Edward McC. Roberts; Bruce M. Collins

[57] ABSTRACT

3-Cyano-4-(2,3-dichlorophenyl)pyrrole is suitable for controlling phytopathogenic microorganisms and is markedly superior in activity to preparation of a similar structure. Said compound may be employed for seed dressing, either along or in the form of compositions.

14 Claims, No Drawings

FUNGICIDAL USE OF A CYANOPYRROLE DERIVATIVE AND METHOD FOR PRODUCING SAME

This is a continuation of Ser. No. 018,689, filed Feb. 25, 1987, now abandoned.

The present invention relates to the use of a cyanopyrrole derivative for controlling phytopathogenic fungi, in particular Botrytis spp., and to the fungicidal use of said compound for seed dressing, as well as to microbicidal compositions, in particular dressing agents, which contain said compound.

Said compound, namely 3-cyano-4-(2,3-dichlorophenyl)pyrrole, is of formula Ia

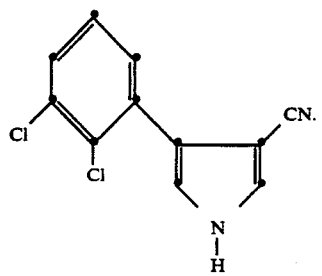

(Ia)

In addition to other 3-cyano-4-phenylpyrrole derivatives, this compound is disclosed in U.S. Pat. No. 4,299,465 as an intermediate for the preparation of N-acetylated pyrrole fungicides. It is stated that the acetylated preparations are excellent fungicides for use against phytopathogenic fungi, whereas the non-acylated intermediates exhibit markedly inferior, i.e. weak, fungicidal activity. This statement is true for the majority of the compounds indicated in this patent. However, it was not recognised that compound Ia deviates entirely from this rule in biologically characteristic manner.

It has been found that the compound of formula Ia employed in the practice of the present invention exerts an unforeseeable high fungicidal activity, in particular against Botrytis spp., and also when used for seed dressing. The compound of formula Ia is therefore distinctly superior to all other 3-cyano-4-phenylpyrrole derivatives disclosed in U.S. Pat. No. 4,299,465 as fungicdal intermediates. Furthermore, the instant fungicidal use of the compound of formula Ia is of additional advantageous economic importance inasmuch as said compound is a precursor of the acetylated final products and therefore simpler and less expensive to produce than they are.

The instant use of the compound of formula Ia is directed in particular against Botrytis spp., which belong to the class of phytopathogenic Fungi imperfecti and which infest a wide range of host plants, e.g. beans, apples, vines, cucumber, lettuce, onions and strawberries. Moreover, further fungi belonging to the above-mentioned class, e.g. Pyricularia and Cercospora, can also be successfully controlled in this manner. A further preferred field of application for the present invention comprises seed dressing, in particular of cereals. In addition to species of cereals such as wheat, rye, barley, oats, rice, maize and sorghum, further cultivated plants suitable for such treatment are e.g. cotton, sugar beet, soybeans, beans and peas. Apart from the aforementioned Fungi imperfecti, further phytopathogenic fungus organisms belonging to the following classes can be successfully controlled by this method of application: Ascomycetes, e.g. Erysiphe, Sclerotinia, Fusarium, Monilinia and Helminthosporium; Basidiomycetes, e.g. Puccinia, Tilletia and Rhizoctonia; and also Oomycetes, e.g. Phytophthora, Plasmopara and Pythium. Special mention should be made of the outstanding activity of compound Ia against Rhizoctonia solani (=sheath blight in rice cultures).

Dressing agents containing 3-cyano-4-(2,3-dichlorophenyl)pyrrole as active ingredient likewise constitute an object of the present invention.

In order to perform the invention, the compound of formula Ia is employed either direct or as active ingredient in agrochemical formulations together with carriers and further adjuvants. The compound of formula Ia can be applied to the crop area, plant or substrate to be treated, simultaneously or in succession, with further compounds. These compounds can be both fertilisers or micronutrient donors or other preparations that influence plant growth. They can also be selective herbicides, insecticides, fungicides, bactericides, nematicides, molluscicides or mixtures of several of these preparations, if desired together with further carriers, surfactants or other application promoting adjuvants customarily employed in the art of formulation.

Suitable carriers and adjuvants can be solid or liquid and correspond to the substances ordinarily employed in formulation technology, e.g. natural or regenerated mineral substances, solvents, dispersants, wetting agents, tackifiers, thickeners, binders or fertilisers.

A preferred method of applying a compound of formula Ia, or an agrochemical composition which contains at least said compound, is foliar application. The number of applications and the rate of application depend on the risk of infestation by the corresponding pathogen (species of fungus). However, the compound of formula Ia can also penetrate the plant through the roots via the soil (systemic action) by impregnating the locus of the plant with a liquid composition, or by applying the compound in solid form to the soil, e.g. in granular form (soil application). In special cases, further types of application are also possible, e.g. selective treatment of the plant stems or buds.

For seed dressing, the compound of formula Ia is applied to the seeds (coating) either by impregnating the seeds with a liquid formulation containing the compound of formula Ia, or by coating them with a solid formulation. Examples of chemical dressing methods which may be selected are immersion dressing, dressing by wetting, short wet dressing, damp dressing, dry dressing and also excess dressing.

For the instant use of 3-cyano-4-(2,3-dichlorophenyl)pyrrole in the form of formulations, said compound is employed together with the adjuvants conventionally employed in the art of formulation. To this end, the compound of formula Ia is formulated in known manner e.g. to emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering, coating or pouring, are chosen in accordance with the intended objectives and the prevailing circumstances. Advantageous rates of application are normally from 50 g to 5 kg of active ingredient (a.i.) per hectare, preferably from 100 g to 2 kg a.i./ha, most preferably from 200 g to 600 g a.i./ha.

The formulations, i.e. the compositions, preparations or mixtures containing the compound (active ingredient) of formula Ia and, where appropriate, a solid or liquid adjuvant, are prepared in known manner, e.g. by homogeneously mixing and/or grinding the active ingredient with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues, e.g. cork powder or sawdust.

Particularly advantageous application promoting adjuvants which are able to reduce substantially the rate of application are also natural or synthetic phospholipids of the series of the cephalins and lecithins. Examples of useful physical forms are phosphatidyl choline mixtures. Examples of synthetic phospholipids are dioctanoylphosphatidyl choline and dipalmitoylphosphatidyl choline.

Depending on the field of application of the compound of formula Ia to be formulated, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyl-trimethylammonium chloride or benzyldi(2-chloroethyl)ethylammonium bromide.

The surfactants customarily employed in the art of formulation are described in publications known to the skilled person.

The agrochemical compositions usually contain 0.1 to 99%, preferably 0.1 to 95%, of a compound of formula Ia, 99.9 to 1%, preferably 99.8 to 5%, of a solid or liquid adjuvant, and 0 to 25%, preferably 0.1 to 25%, of a surfactant.

Whereas commercial products will preferably be formulated as concentrates, the end user will normally employ dilute formulations.

The compositions may also contain further auxiliaries such as stabilisers, antifoams, viscosity regulators, binders, tackifiers as well as fertilisers or other active ingredients for obtaining special effects.

As described in the literature (q.v. e.g. Tetrahedron Letters (1972) 5337), 3-cyano-4-(2,3-dichlorophenyl)-pyrrole can be prepared in accordance with the following reaction scheme:

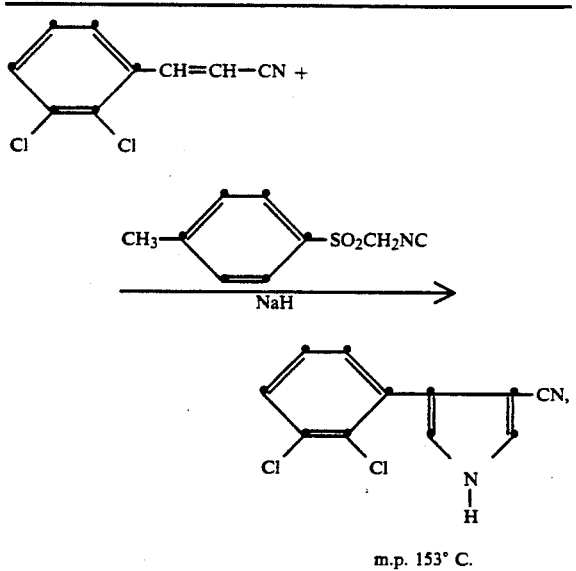

m.p. 153° C.

Formulation examples for the active ingredient of formula Ia
(throughout, percentages are by weight)

| Example 1: Wettable powders | a) | b) | c) |
|---|---|---|---|
| compound of formula Ia | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7-8 moles of ethylene oxide) | — | 2% | — |
| highly dispersed silicic acid | 5% | 10% | 10% |
| kaolin | 62% | 27% | — |

The active ingredient is thoroughly mixed with the adjuvants, and the mixture is thoroughly ground in a suitable mill, affording wettable powders which can be diluted with water to give suspensions of the desired concentration. Such suspensions can be sprayed onto the cereal seeds. They can also be employed for foliar application to the plant.

| Example 2: Emulsifiable concentrate | |
|---|---|
| compound of formula Ia | 10% |
| octylphenol polyethlene glycol ether (4-5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water. Seeds of any type can be wetted with these emulsions.

| Example 3: Dusts | a) | b) |
|---|---|---|
| compound of formula Ia | 5% | 8% |
| talcum | 95% | — |
| kaolin | — | 92% |

Ready-for-use dusts are obtained by mixing the active ingredient with the carriers, and grinding the mixture in a suitable mill. Such dusts are suitable for the dry dressing of cereal seeds.

| Example 4: Extruder granulate | |
|---|---|
| compound of formula Ia | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| Example 5: Coated granulate | |
|---|---|
| compound of formula Ia | 3% |
| polyethylene glycol (mol. wt. 200) | 3% |
| kaolin | 94% |

The finely ground active ingredient is uniformly applied, in a mixer, to the kaolin moistened with polyethlene glycol. Non-dusty coated granulates are obtained in this manner. If after a certain time cereal seeds are placed in the same mixer, then coated seeds are obtained in the same operation.

| Example 6: Suspension concentrate | |
|---|---|
| compound of formula Ia | 40% |
| ethylene glycol | 10% |
| nonylphenol polyethylene glycol (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water. Such suspensions are suitable for foliar application and for seed dressing (immersion dressing, spray dressing).

Dressing by Wetting

In closable plastic beakers, 80 g of dry cereal seeds (e.g. maize) are thoroughly mixed with 3-cyano-4-(2,3-dichlorophenyl)pyrrole in the form of an aqueous suspension, emulsion or solution. The substance is applied at such a rate that an active ingredient concentration of 0.06 to 0.001%, based on the dry weight of the maize, is achieved.

BIOLOGICAL EXAMPLES

EXAMPLE 1

Action against *Botrytis cinerea* on Apples

Artificially damaged apples are treated by dropping a spray mixture (0.006% of active ingredient) prepared from a wettable powder formulation of the test compound onto the injury sites. The treated fruit is then inoculated with a spore suspension of *Botrytis cinerea* and incubated for 1 week at high humidity and about 20° C. Evaluation is made by counting the number of injury sites attacked by rot and deducing the fungicidal action of the test compound therefrom. Compared with untreated controls (100% attack), the compound of formula Ia inhibits fungus attack almost completely (less than 5% attack).

EXAMPLE 2

Action against *Pyricularia oryzae* on Rice

After a cultivation period of 2 weeks, rice plants are sprayed with a spray mixture (0.02% of active ingredient) prepared from a wettable powder formulation of the test compound. After 48 hours the treated plants are infected with a conidia suspension of the fungus. Evaluation of fungus attack is made after incubation for 5 days at 95-100% relative humidity and 24° C. The compound of formula Ia inhibits Pyricularia attack markedly. It reduces attack to less than 10%.

EXAMPLE 3

Action against *Cercospora arachidicola* on Groundnut Plants a) Residual protective action Groundnut plants 10-15 cm in height are sprayed with a spray mixture (0.02% of active ingredient) prepared from a wettable powder formulation of the test compound, and infected 48 hours later with a conidia suspension of the fungus. The infected plants are incubated for 72 hours at about 21° C. and high humidity and then stood in a greenhouse until the typical leaf specks occur. Evaluation of the fungicidal action is made 12 days after infection and is based on the number and size of the specks.

b) Systemic action

Groundnut plants 10-15 cm in height are sprayed with a spray mixture (0.006% of active ingredient, based on the volume of the soil) prepared from a wettable powder formulation of the test compound. The treated plants are infected 48 hours later with a conidia suspension of the fungus and then incubated for 72 hours at about 21° C. and high humidity. The plants are then stood in a greenhouse and evaluation of fungus attack is made 11 days later.

Compared with untreated and infected control plants (number and size of the specks=100%), Cercospora attack on groundnut plants treated with the compound of formula Ia is reduced to less than 10%.

EXAMPLE 4

Action against *Helminthosporium gramineum*

Wheat grains are contaminated with a spore suspension of the fungus and dried. The contaminated grains are dressed with a suspension of the test compound prepared from a wettable powder (600 ppm of active ingredient, based on the weight of the seeds). Two days later the grains are placed in suitable agar dishes and a count of the fungus colonies which have developed around the grains is made after another 4 days. The effectiveness of the test compound is assessed on the basis of the number and size of the colonies. The compound of formula Ia inhibits fungus attack substantially (0 to 10%).

EXAMPLE 5

Action against *Fusarium nivale*

Wheat grains are contaminated with a spore suspension of the fungus and dried. The contaminated grains are dressed with a suspension of the test compound prepared from a wettable powder (600 ppm of active ingredient, based on the weight of the seeds). Two days later the grains are placed in suitable agar dishes and a count of the fungus colonies which have developed around the grains is made after another 4 days. The effectiveness of the test compound is assessed on the basis of the number and size of the colonies.

The development of fungus colonies is almost completely inhibited (0 to 5%) on wheat grains treated with a wettable powder formulation containing as active ingredient the compound of formula Ia.

EXAMPLE 6

Action against *Tilletia tritici*

Barley grains are contaminated with a spore suspension of the fungus and dried. The contaminated grains are dressed with a suspension of the test compound prepared from a wettable powder (600 ppm of active ingredient, based on the weight of the seeds). Two days later the grains are placed in suitable agar dishes and a count of the fungus colonies which have developed around the grains is made after another 4 days. The effectiveness of the test compound is assessed on the basis of the number and size of the colonies. The compound of formula Ia inhibits fungus attack substantially (0 to 10%).

EXAMPLE 7

Action against *Botrytis cinerea*, *Fusarium nivale*, *Helminthosporium teres* and *Monilinia fructicola* (Agar Incorporation Test)

The test compound is carefully incorporated into a sterile liquid agar nutrient medium which has been cooled to 50° C., and the medium is then placed into petri dishes. The concentrations are based on the amount of active ingredient (in ppm) in the nutrient medium. After the nutrient medium has congealed, the dishes are inoculated at the centre with an agar disc of about 6 mm $\phi$ which is covered with fungi. These agar discs are punched out of a petri dish culture of the test fungus with a cork borer and placed upside-down onto the treated agar plate.

The inoculated dishes are incubated at 20°-24° C. in the dark.

As soon as the growing fungus in the parallel control dish (containing no active ingredient) has covered three quarters of its agar surface, the level of mycelium growth in the treated dishes is marked, and the further growth in these dishes is then controlled daily. The values are plotted on semi-logarithmic millimeter graph paper. The EC-50 values are then read off from this graph, i.e. the active ingredient concentration is determined at which 50% fungus growth inhibition is achieved.

All 3-cyano-4-phenylpyrrole derivatives disclosed in U.S. Pat. No. 4,229,465) were tested comparatively with respect to their action against the above fungi. The active ingredient concentrations in the nutrient media were 100 ppm, 10 ppm, 1 ppm, 0.1 ppm and 0.01 ppm (100 ppm=0.01% a.i.).

The compounds of the formula (numbered according to the details in the literature)

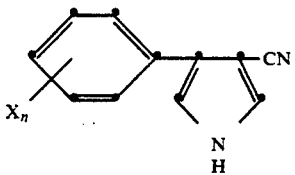

| No. | $X_n$ | m.p. [°C] |
|---|---|---|
| 8 | H | 129-131 |
| 9 | 2-Cl | 137-139 |
| 10 | 3-Cl | 147 |
| 11 (=Ia) | 2,3-Cl$_2$ | 153 |
| 12 | 2-CF$_3$ | 105-107 |
| 13 | 2-Br | 145 |
| 14 | 2-CH$_3$ | 115-118 | were used against the various fungi. The following EC-values were obtained:

| | EC-50 Values in ppm a.i. | | | | | | |
|---|---|---|---|---|---|---|---|
| | Compound | | | | | | |
| Fungus | 8 | 9 | 10 | 11 | 12 | 13 | 14 |
| B. cinerea | 10.0 | 1.1 | 0.9 | 0.7 | 1.0 | 1.5 | 3.4 |
| F. nivale | 15.0 | 2.0 | 1.9 | 0.36 | 0.8 | 0.85 | 3.0 |
| H. teres | 15.0 | 4.5 | 1.8 | 0.75 | 3.0 | 2.3 | 9.0 |
| M. fructicola | 3.0 | 1.0 | 1.7 | 0.6 | 0.8 | 1.4 | 1.8 |

It can be seen that among the 3-cyano-4-phenylpyrrole derivatives known from the literature, only in the case of one single compound, namely No. 11, i.e. compound Ia of the present invention, are inhibition values obtained at an unusually low active ingredient concentration. All remaining compounds have to be employed at distinctly higher concentrations to achieve the same results.

What is claimed is:

1. The method of controlling phytopathogenic fungi systemically in a plant which comprises applying to the soil at the locus of the plant's growth a liquid or solid composition containing a fungicidally effective amount of a compound of the formula:

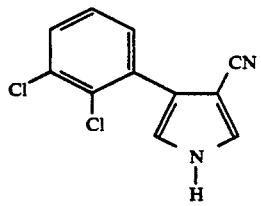

and at least one carrier for said compound.

2. The method according to claim 1 wherein the phytopathogenic fungi is Fungi imperfecti.

3. The method according to claim 1 wherein the phytopathogenic fungi is Botrytis.

4. The method according to claim 1 wherein the phytopathogenic fungi is of the class Ascomycetes.

5. The method according to claim 4 wherein the fungi is a Fusarium species.

6. The method of controlling phytopathogenic fungi in plant seeds which comprises coating or impregnating the seeds with a liquid or solid composition containing a fungicidally effective amount of a compound of the formula:

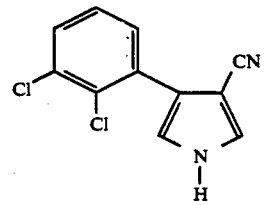

and at least one carrier for said compound.

7. The method according to claim 6 wherein the phytopathogenic fungi is *Fungi imperfecti.*

8. The method according to claim 6 wherein the phytopathogenic fungi is Botrytis.

9. The method according to claim 6 wherein the phytopathogenic fungi is of the class Ascomycetes.

10. The method according to claim 9 wherein the fungi is a Fusarium species.

11. A dressed seed having reduced susceptibility to phytopathogenic fungi which is coating or impregnating with a liquid or solid composition containing a fungicidally effective amount of a compound of the formula:

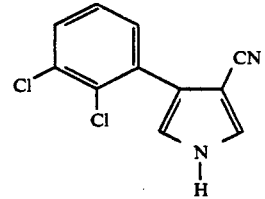

and at least one carrier for said compound.

12. A dressed seed according to claim 11 which is a bean, apple, vine, cucumber, lettuce, onion, strawberry, cereal, cotton, sugar beet, soybean, or pea seed.

13. A dressed seed according to claim 11 which is a wheat, rye, barley, oat, rice, maize, or sorghum seed.

14. A dressed seed according to claim 11 which is a cereal seed.

* * * * *